(12) United States Patent
Bala (10) Patent No.: US 10,905,322 B2
(45) Date of Patent: Feb. 2, 2021

(54) BALA LAPAROSCOPE SYSTEM

(71) Applicant: John L. Bala, Hollywood, SC (US)

(72) Inventor: John L. Bala, Hollywood, SC (US)

( * ) Notice: Subject to any disclaimer, the term of this patent is extended or adjusted under 35 U.S.C. 154(b) by 0 days.

(21) Appl. No.: 16/365,183

(22) Filed: Mar. 26, 2019

(65) Prior Publication Data
US 2020/0305703 A1    Oct. 1, 2020

(51) Int. Cl.
| | | |
|---|---|---|
| *A61B 1/00* | (2006.01) | |
| *A61B 1/313* | (2006.01) | |
| *A61B 1/018* | (2006.01) | |
| *A61B 1/12* | (2006.01) | |
| *A61B 1/06* | (2006.01) | |
| *A61B 1/07* | (2006.01) | |
| *A61B 1/04* | (2006.01) | |

(52) U.S. Cl.
CPC ........ *A61B 1/3132* (2013.01); *A61B 1/00103* (2013.01); *A61B 1/00197* (2013.01); *A61B 1/018* (2013.01); *A61B 1/04* (2013.01); *A61B 1/0661* (2013.01); *A61B 1/07* (2013.01); *A61B 1/126* (2013.01)

(58) Field of Classification Search
None
See application file for complete search history.

(56) References Cited

U.S. PATENT DOCUMENTS

| | | | | |
|---|---|---|---|---|
| 5,261,889 A * | 11/1993 | Laine | ..................... | A61B 1/015 600/104 |
| 5,402,768 A * | 4/1995 | Adair | ................. | A61B 1/00073 600/106 |
| 5,575,756 A * | 11/1996 | Karasawa | .......... | A61B 1/00068 600/121 |
| 5,957,832 A * | 9/1999 | Taylor | ................ | A61B 1/00149 600/114 |
| 6,126,592 A * | 10/2000 | Proch | ................. | A61B 1/00091 600/114 |
| 2002/0007111 A1* | 1/2002 | Deckert | ............. | G02B 23/2469 600/177 |
| 2007/0066869 A1* | 3/2007 | Hoffman | ............ | A61B 1/00135 600/121 |
| 2009/0036744 A1* | 2/2009 | Vayser | ............... | A61B 1/00096 600/182 |
| 2009/0264706 A1* | 10/2009 | Bala | .................... | A61B 1/00101 600/160 |
| 2011/0292195 A1* | 12/2011 | Dahmen | ............ | A61B 1/00183 348/68 |
| 2012/0316394 A1* | 12/2012 | Yoshida | ............ | A61B 1/00091 600/123 |

* cited by examiner

*Primary Examiner* — Timothy J Neal (57) ABSTRACT

The Bala Laparoscope System is a reusable and/or disposable embodiment of a modular, surgical laparoscope with removable interchangeable viewing angles that enable one laparoscope to be used in place of two separate conventional laparoscopes with different viewing angles. The invention provides for distal lens cleaning without removing the laparoscope from the body. In addition, the invention provides for integrated image-guided working channels for surgical tools; cauterization and laser ablation and internal drug delivery. The simplicity of its optical design allows a much longer useful instrument life than conventional laparoscopes and essentially eliminates the need to rebuild them.

14 Claims, 8 Drawing Sheets

BALA LAPAROSCOPE SYSTEM

BACKGROUND OF THE INVENTION

Laparoscopes are devices used in the field of medicine that allow visual examination inside of the body cavity for examining organs and tissue; for diagnostic sampling of tissue; for safe manipulation of instruments; and, for performing minimally invasive surgery. Laparoscopes are primarily used in abdominal and urological procedures. The elements of a laparoscope include an optical telescope for viewing the image from inside of the body cavity and a means for illuminating the area viewed by the telescope. There are numerous telescope designs most of which use a combination of lenses and glass rods to transmit the image from the body cavity to a viewing eyepiece. In recent years, use of the eyepiece has been replaced with highly sophisticated electronic cameras with the images displayed in real time on a video monitor.

Illumination of the body is classically performed by a fiber optic bundle comprised of thousands of small diameter optical fibers formed into a bundle that surround the telescope. A high powered external light source provides illumination through a fiber optic light transmitting cable connects to a fiber optic ferrule at the proximal end in the laparoscope.

The most commonly used laparoscopes are symmetrical about their optical center (i.e. a zero degree laparoscope). Typically, the telescopes use 20-24 lenses and glass rods to relay an image from within the body cavity to a viewing eyepiece located outside the body. Each lens element requires complex anti reflection coating to reduce surface reflection losses. Normal reflection loss from an uncoated lens is approximately 8% transmission loss per lens. The reflection losses are cumulative. Thus, very little, if any, of an image would be seen through the telescope without efficient anti-reflection coatings.

The complexity of a disposable laparoscope optical lens and rod system with multi-layer anti reflective coatings have made either the cost or performance unattractive in the marketplace. Substitutions of plastic lenses in place of glass coupled with complex vacuum deposited multi layer anti-reflective coatings for 20-24 lens and rods, with associative spacers together with fiber optic assembly have made attempts at a marketable disposable laparoscope unsuccessful.

The embodiment of Bala Laparoscope System invention involves a different approach for a laparoscope that make either a reusable or disposable embodiment practical from a cost and performance perspective. Fundamentally the Bala Laparsocope System utilizes two achromats and three singlet lenses for the telescope image acquisition. An eyepiece requires an additional achromat. A single layer magnesium fluoride coating is sufficient to provide a bright, sharp visual image. The image quality and brightness is comparable to laparoscopes on the market today.

The embodiment of the Bala Laparoscope System involves separating the illumination pathway into two separate parts. The first path is part of the proximal housing consisting of microscopic fiber optics that individually surround the telescope, to form a halo light ring and bundled together at the ferrule.

The second part of the illumination pathway uses the same individual microscopic fiber optics sandwiched between two cylinders creating an Illumination Adapter. The adapter slides over the telescope and makes direct contact to the light halo ring. Separating the illumination fiber optics into two parts enables the Illumination Adapters to become interchangeable. In one embodiment, the adapter is at the same zero degree angle as the telescope.

An Illumination Adapter having a prism and angled fiber optics at the distal end changes the viewing angle of the telescope. Conventional laparoscopes use a separate zero degree laparoscope for on axis viewing and a completely different laparoscope for angular views. Typically, a surgeon will use both a zero degree and a 30 degree laparoscope for many surgical procedures. The embodiment of the Bala Laparoscope System uses one telescope and interchangeable Illumination Adapters for different viewing angles. Furthermore, in the embodiment, the angled illumination adapters can be continuously rotated 360 degrees.

In terms of physical size, construction, and user interface, the Bala Laparoscope System would seem very familiar to today's surgeons. However, the similarity ends when the surgeon requires a different viewing angle. Currently the surgeon must stop the procedure, remove the laparoscope from the body and change to a completely different instrument. This requires unplugging the light cable and camera from the device in use and re-plugging them into a different laparoscope, then, re-entering the body cavity with the new scope, refocusing it and re-orient the scope to the surgical site. Although this can be done reasonable quickly with experience, it still requires time in which the surgeon is not occupied with the patient, but with the equipment. The embodiment of the Bala Laparoscope System requires, removing the scope from the body, interchange Illumination Adapters and re enter the body to continue the procedure.

The embodiment of disposable the Bala laparoscope System uses a variation of the reusable laparoscope design to create a single use disposable laparoscope. Material and construction changes are used to reduce the cost, but the device functions identically. The disposable laparoscope uses the same lens optical design, but substitutes plastic lenses for the singlet elements in place of glass lenses.

The embodiment of the disposable laparoscope as a single use device is pre packaged and pre sterilized in a sterile pouch. The invention postulates the package will be sealed and ETO sterilized through the pouch prior to shipping and opened by the surgical staff just prior to use. Furthermore, the device cannot be re sterilized by means of autoclaving, as this process will distort the plastic materials used in the construction which prevents its re use. At the completion of a surgical procedure the laparoscope is disposed of in approved medical waste. The embodiment eliminates the need for post, surgery clean up of the laparoscope.

The disposable laparoscope system uses the same split illumination system as the reusable laparoscope. However, in the preferred embodiment of the disposable laparoscope, clear cylinders (lumens) made of an optical grade plastic which functions in place of glass fiber optic adapters. In the preferred embodiment the plastic lumen provides a means of cleaning the telescope distal objective lens without removing the laparoscope from the body. Other disposable variations of the plastic lumen provide the ability to perform image directed therapeutic drug delivery and working channels that combine imaging and therapy. The disposable Lumen Adapters are compatible with both the disposable and reusable laparoscope.

SUMMARY OF THE BALA LAPAROSCOPE INVENTION

The embodiment of Bala Laparoscope System telescope is a reusable laparoscope designed with two achromats and three singlet lenses for image acquisition and one achromat for an, eyepiece.

In the preferred embodiment the telescope glass lenses in the Bala Laparoscope System are coated with magnesium fluoride anti reflection coating, Conventional laparoscopes with 20-24 lenses and rods utilize complex multi-layer evaporated coatings required for higher light transmission to achieve acceptably bright images. However, the embodiment of the Bala Laparoscope System does not preclude the use of other anti reflective coatings.

Because the Bala Laparoscope System uses fewer lenses, magnesium fluoride provides more than adequate brightness and is a more resilient than multi-layer evaporated coatings, Most laparoscope failures result from the heat and humidity of the autoclave sterilization process. The Bala Laparoscope System with fewer lens and a more robust coating is less susceptible to the autoclave process. Typically, 500 procedures per/scope for the Bala Laparoscope System are possible, compared to the 75-100 per/scope surgeries typical for conventional laparoscopes.

The embodiment of the Bala Laparoscope System eliminates the requirement for an eye piece. Conventional laparoscopes designed with an eyepiece require an auxiliary optical system such as an endo coupler, or other similar optical device, to interface with a video camera. The endo coupler focuses an image from the eyepiece onto a camera's photo sensitive surface; the image is then displayed onto a video monitor. An endo coupler is a costly optical element that must be re sterilized after each use. In modern operating rooms, human eye viewing is seldom, if ever used, as video monitors have supplanted viewing through an eyepiece.

In the preferred embodiment, the Bala Laparoscope System eliminates both the endo coupler and eyepiece, by focusing, the telescope image directly onto a video camera This is accomplished using a "C" mount adapter for mounting a camera onto the telescope output. The mounting adapter also functions as a means of adjusting the camera focus. However, some users may be uncomfortable with elimination of the eyepiece; therefore, in one embodiment, the Bala Laparoscope System incorporates an optional eyepiece with the telescope.

In the preferred embodiment, the proximal end of the Illumination Adapter directly contacts the light halo ring and mechanically interlocks to the proximal housing. The distal end of the Illumination Adapter terminates with a zero power lens or an angled prism to hermetically seal the adapter. Illumination Adapters are interchangeable by sliding them over the telescope. The embodiment uses one telescope and multiple interchangeable Illumination Adapters for different viewing angles rather than a separate laparoscope for each angle, thereby, eliminating changing light cables or cameras.

In the preferred embodiment, an external light source is connected to a ferrule on the laparoscope. The ferrule brings the light from an external source to the circular light, halo ring surrounding the telescope at the proximal end and interfaces with the Illumination Adapter completing the light path through the laparoscope into the body. A flange on the Illumination Adapter interlocks with the proximal housing insuring that the Illumination Adapter is in direct contact with the light halo ring.

The embodiment of reusable Illumination Adapters are constructed from a core of many individual microscopic fiber optics sandwiched between two cylinders with an inner core diameter that slides over the telescope and interfaces with a light halo ring. The fibers are cemented at each end and ground and polished to create an even illumination pattern in the body cavity.

In the preferred embodiment, the Bala Laparoscope System embodies interchangeable prisms to change the angle of view of the Illumination Adapters from 0, 30 or 45 degrees. At the distal end the adapters the telescope contacts the prisms to change the acceptance angle of the telescope to match that of the prism. The preferred embodiment of 0, 30 and 45 degree Illumination Adapters are consistent with those normally used with laparoscopes, however, different prisms can, be used with the Bala Laparoscope System for other angles.

Conventional laparoscope designs include two major construction problems not conducive to rendering them candidates for a single use medical devices. The telescope and the illumination system each requires major technical changes in order to reduce cost without reducing image quality or performance. The Bala Laparoscope System embodiment achieves these objectives in addition to adding new capability that is not available with conventional laparoscopes.

The preferred embodiment of the Bala Laparoscope System, the disposable laparoscope addresses the cost of the telescope system with the use of two achromats and three singlet lenses instead of the 20 to 25 optical elements necessary with a conventional laparoscope. Furthermore, plastic lenses can be substituted for the three singlet glass, lenses used with the reusable laparoscope with the same magnesium fluoride coating.

In the preferred embodiment of the disposable laparoscope, Poly Ether Ether Ketone (PEEK) is the material of choice for the construction of the lens tube in place of stainless steel. PEEK has high strength, chemical resistance and heat tolerance. In addition, it can easily be pigmented to be light absorbing to reduce stray light within the telescope. For the same reasons PEEK it is used for the lens spacers. The spacers also add strength to the telescope's structural integrity.

In the preferred embodiment, the proximal assembly is also constructed of PEEK material designed in a clam cell configuration. The two halves of the clam shell encompass a light halo ring and ferrule connector and provide for a camera mount with a focus adjustment means. The proximal assembly clam shell is cemented together and to the lens tube to complete the telescope assembly.

A light halo ring is constructed of Nippon Zeon 5000, a cyclic Polyolefin, an optical grade plastic that achieves a 93% optical transmission. This grade of plastic material is used because the plastic cannot survive the autoclave process and distorts in the sterilization process, thus, preventing reuse.

The Bala Laparoscope System uses plastic cylinder lumens in place of the fiber optics for illumination with the reusable adapters. The embodiment of the Bala Laparoscope System uses a cylinder of high index, high transmission plastic (Nippon Zeon 5000, Cyclic Polyolefin) as the core and air as the low refractive index cladding, providing the same total internal reflection phenomena as with glass fiber optics. However, the glass fibers have a higher Numerical Aperture and are more efficient than the plastic material and is lower in transmission, To compensate, the embodiment of the plastic disposable Lumen Adapter requires increasing the light output of the external light source and diffusing the distal end of the lumen to expand the area of illumination.

The embodiment of the Bala Laparoscope System allows the plastic lumen adapters to be used interchangeably with reusable ones on either the disposable or reusable telescopes and both have 0, 30 and 45 degree prisms that interface with the telescope for angular viewing. Furthermore, each adapter can be rotated continuously 360 degrees, unlike conventional fixed angled laparoscopes that have limited practical rotational capability. The plastic Lumen Adapters have the advantage of being an extruded cylinder which permit greater flexibility to expand the applications of the laparoscope's capabilities beyond a visual only device.

In the preferred embodiment, the disposable plastic Lumen Adapters are designed to clean the objective lens without removing the laparoscope from the body. This is accomplished by means of a 0.5 mm clear pathway traversing the length of the Lumen Adapter between its inner and out diameters.

A self-sealing diaphragm located at the proximal end of the adapter provides a means for injecting Saline or other suitable cleaning solution with a syringe through the 0.5 mm pathway adapter to the distal objective lens. A diaphragm molded into the flange housing the adapter prevents the Saline from escaping when it is being injected at the proximal input.

In the embodiment, a deflector located at the distal end of the lumen disperses the Saline over the objective lens to remove blood and tissue that may have adhered to the lens. As a fact of the process, injecting the Saline into the lumen first displaces the air present in the lumen. This air is under pressure as it is being displaced with fluid. The air pressure caused by the syringe injection blows away solid particulate, while the fluid that follows washes the objective lens.

In another embodiment, a plastic Lumen Adapter is used to deliver internal drug therapy through a hypodermic needle located at the distal end. The drug is injected into the diaphragm at the proximal end, sent the length of the 0.5 mm channel to the distal end. The injection is image-guided and enables the surgeon to remove the air from the pathway before locating the injection site with the telescope video image.

In one embodiment, the disposable Lumen Adapters have working channels for purposes of using the laparoscope beyond its typical use of visual examination and examining organs and tissue. The working channels allow therapeutic surgery using the laparoscope. The working channels enable a laser ablation fiber or surgical tool to be delivered through the lumen in a direct pathway into the body. The laparoscope visually directs a laser or working tool, eliminating the need for an additional entry port into the body. A diaphragm integrated into the proximal end of the lumen prevents back flow of particulate or fumes from exiting during surgery. The lumen can also be used to evacuate smoke, fumes and particulate post surgery. The disposable Lumen Adapters are not restricted to a single working channel Additional working channels can be provided that fit the trocar opening.

By combining imaging and therapeutic functions into one instrument, the disposable lumens address the need for an instrument which not only provides an economic imaging means for performing laparoscopic surgery, but provides the surgeon with access to new capabilities that are not provided by conventional laparoscopes.

DETAILED DESCRIPTION OF THE INVENTION

Figure 1:
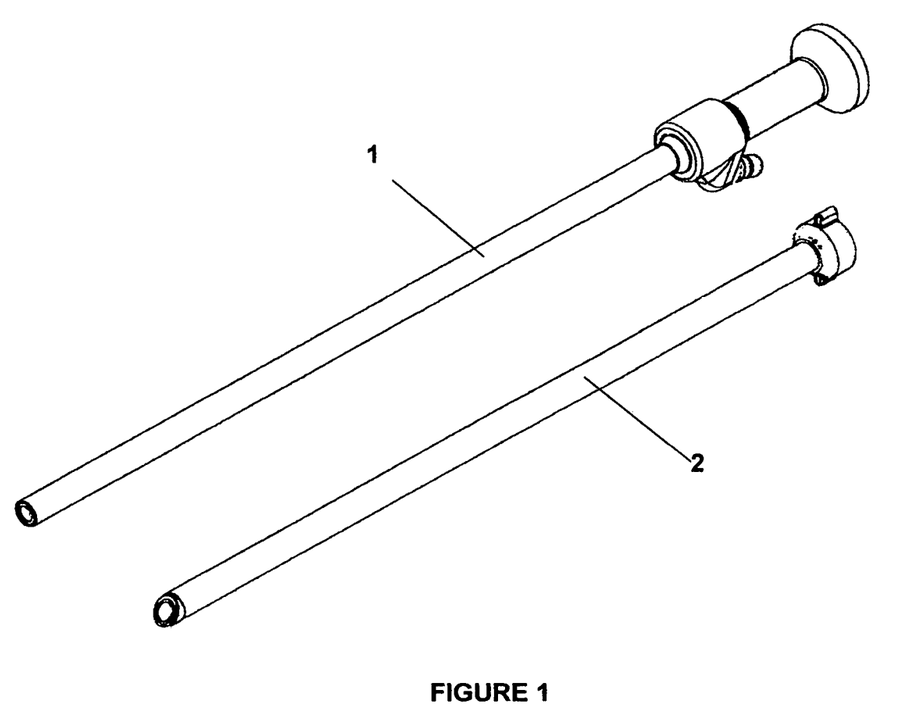
FIG. 1 is an orthogonal view of the embodiment of the Bala Laparoscope System with interchangeable Illumination Adapters.

A preferred embodiment of the invention illustrated in FIG. 1 is a laparoscope consisting of two separate elements, a telescope 1 and interchangeable illumination adapters 2.

The illustration of the telescope 1 is shown with an eyepiece for either human viewing or connection to a video camera for viewing with a video monitor. The telescope 1 has several embodiments: In one embodiment the telescope is reusable and utilizes an eyepiece. In a second embodiment, a reusable telescope 1 eliminates the eyepiece and utilizes a direct electronic camera adapter. In a third embodiment, the telescope 1 is disposable with an eyepiece. In a fourth embodiment, the telescope 1 is disposable without the eyepiece.

When using a video camera with the laparoscope 1, a separate auxiliary optical device attached to the eyepiece is required to capture the image and refocus it onto a video camera. The auxiliary optical device and video camera are not shown in the illustration as it is established art.

Illumination adapters 2 are interchangeable light transmitters that slide over the body of the telescope 1 to transmit illumination light from the proximal end to the distal end of the telescope 1 to complete the laparoscope for its intended use.

In the embodiment, the Illumination Adapter 2 also has other embodiments consisting of different angles, light transmission materials, drug delivery means, lens cleaning and working channels.

Figure 2:
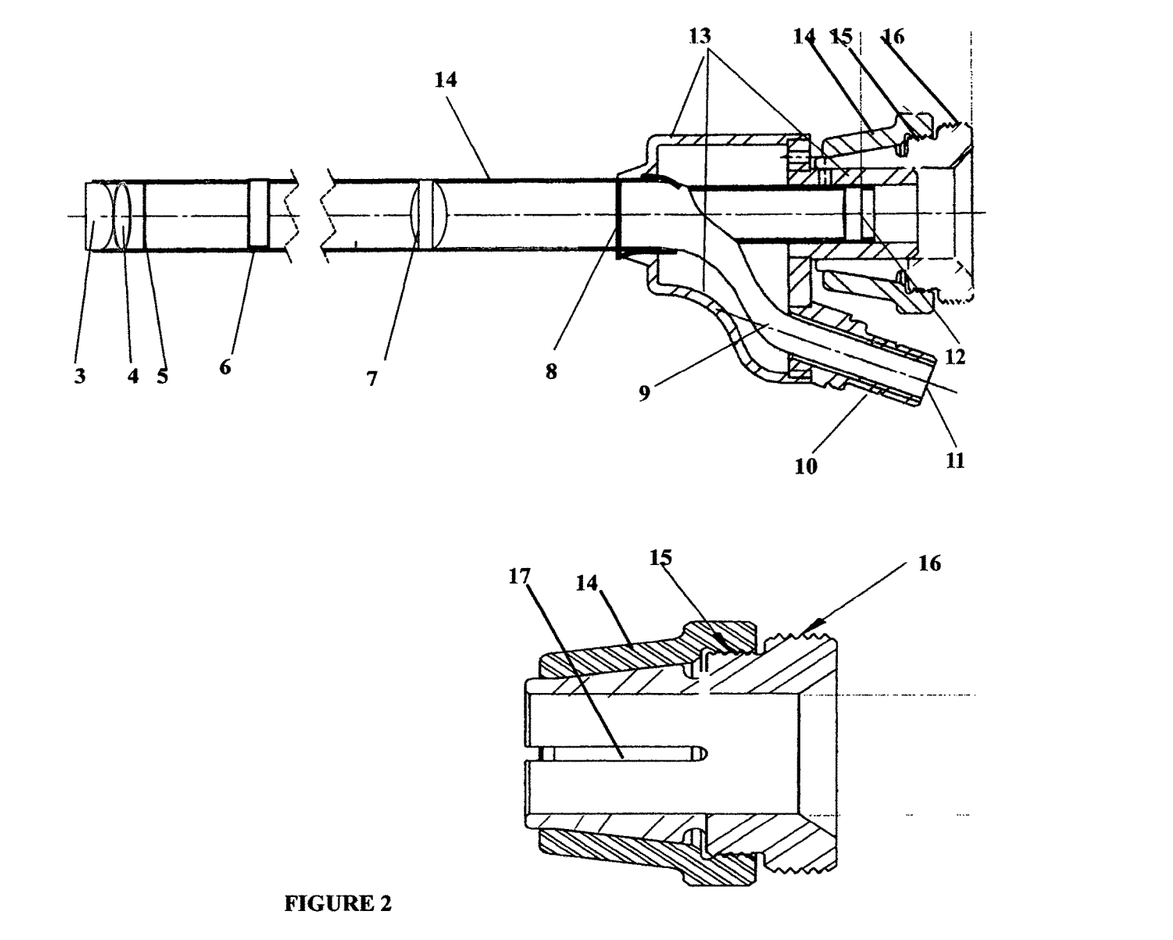
FIG. 2 is a lateral view of the telescope with a view of an embodiment without an eyepiece.

FIG. 2 is a lateral view that describes the preferred embodiment of the telescope 1 optical, system and its physical assembly that is approximately 307 mm in length, Lens #1 3 is an achromatic doublet objective lens, used in conjunction with Lens #2, 4 a singlet comprise the objective lens system. A field stop 5 is located 5 mm from the objective lens #2 4. Lens #3 6 a singlet lens, is the first of a series of relay lenses and located 50 mm from the field stop 5. Lens #4, 7 is an achromatic doublet lens that relays the image from lens #3 6 to lens #4 7 a distance of 115 mm Lens #4 7 relays the image 116 nm to lens #5 12, a singlet at the exit of the optical system. In the preferred embodiment all lenses are anti reflection coated with magnesium fluoride. Anti reflection coatings with equal or greater performance would be acceptable.

In one embodiment of the fiber optic illumination system, light from an external source 11 is directly transmitted to the fibers in a ferrule 10 creating an assembly of bundled fibers 9 which create a light halo ring of fibers 8 around the telescope tube 14 and are encapsulated by the proximal housing 13.

In one embodiment, the proximal assembly provides the means to connect the telescope housing 13 directly a video camera, eliminating the eyepiece by means of a threaded focusing assembly consisting of parts 14, 15, 16 and 17. A video camera "C" mount 16 on the assembly is threaded onto a video camera that slides over the proximal housing 13. The focusing assembly slides back and forth on the housing as a focusing adjustment.

In the preferred embodiment, releasing the pressure on the C mount taper 17 by turning the locking mechanism 14 counterclockwise allows the assembly to slide in an out to visually focus the camera by an image on a video monitor. Turning the the locking mechanism clockwise 14 causes the threads on the focus assembly 15 to apply pressure to a split taper 17 clamping the C mount to the proximal housing 13, thus, locking the camera in place. Other embodiments can provide a similar means of adjusting a camera's focus.

Figure 3:
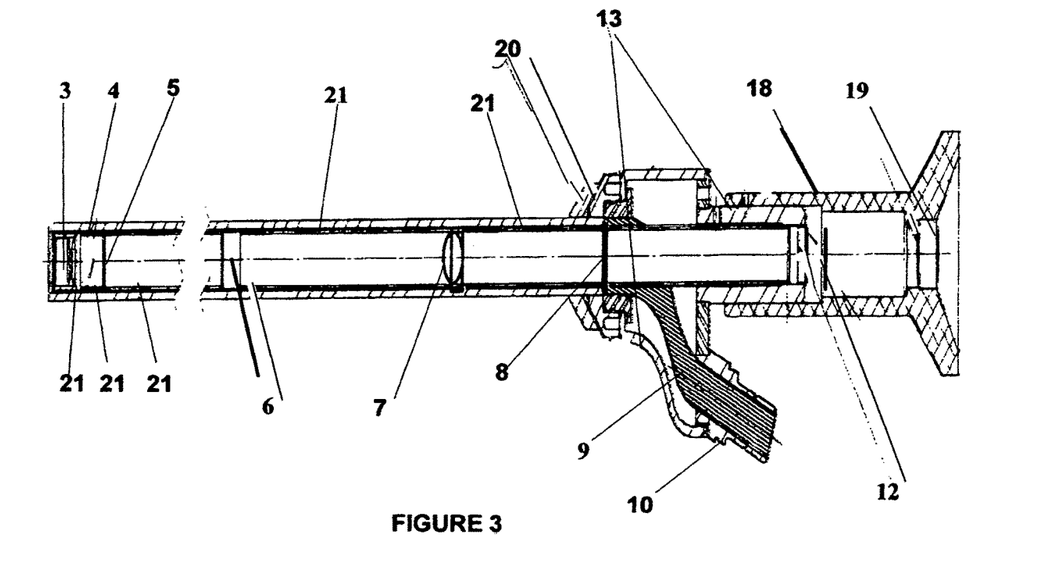
FIG. 3 Is a lateral view of the laparoscope with an eyepiece.

FIG. 3 is a lateral view that shows an embodiment of the telescope with a eyepiece configuration 18, attached to the proximal housing 13. The eyepiece assembly 18 is constructed with achromatic doublet lens 19 and is focused by sliding the eyepiece assembly 18 onto the proximal assembly 13 until the best possible image is achieved. Prior to insertion of the eyepiece 18, a quick drying cement or epoxy is applied to the proximal assembly 13 and the core of the eyepiece 18 and secured until the cement is cured. The illustration also indicates the different spacers 21 between lenses 3,4, the field stop 5 and lens 6,7 and 12. The embodiment the illumination system is identical to 8,9,10, 11,13 &14 of FIG. 2.

Figure 4:
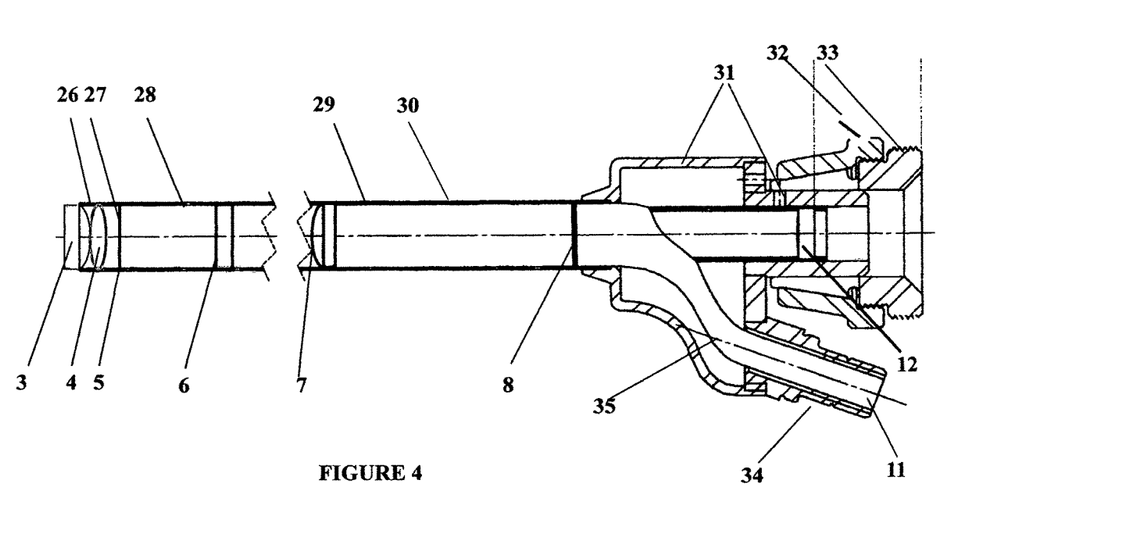
FIG. 4 Is a lateral view of the disposable telescope without an eyepiece.

FIG. 4 is a lateral view illustrates a disposable embodiment of the telescope 1. In the embodiment, the telescope consists of glass lenses #1 3, lens #2 4, field stop 5, lens 6, lens 7 and 12. In the preferred embodiment, the spacers 26, 27, 28, 29 and 30 between lenses are made of black pigmented Poly Ethel Ethel Ketone (PEEK). In a preferred embodiment, the lens tube 14 that retains the optical and spacer components is also made of PEEK material, but is pigmented for aesthetic purposes.

In the preferred embodiment, the light halo ring is constructed of a high transmission optical plastic, preferably Nippon Zeon 5000 cyclic polyolefin that is injection molded as a two piece assembly to surround the lens tube 14 to create a light halo 8 at the proximal assembly 31. The two piece illumination assembly 35 is cemented together, with, an index matching cement to construct a singular assembly around the lens tube 29. The preferred plastic material Nippon Zeon 5000 is selected for the illumination assembly 35 because of the plastic's high optical transmission properties and its ability to distort at autoclave temperatures, preventing the reuse of the telescope assembly for medical purposes. Other equivalent plastics materials of equal or greater performance would be acceptable.

In the preferred embodiment, the proximal body component is of a two piece clam shell 31 construction with the ferrule 34 and illumination assembly 35 integrated into the clam shell. In an embodiment, the camera mounting assembly components, 32 and 33 are of molded PEEK construction. In the embodiment increasing, pressure by tightening assembly 32 forces the segmented taper of 33 to clamp against the proximal body 31 to retain camera focus position. Releasing the pressure on assembly 32 allows assembly 33 to slide to a new focus without a separate auxiliary optical system.

Figure 5:
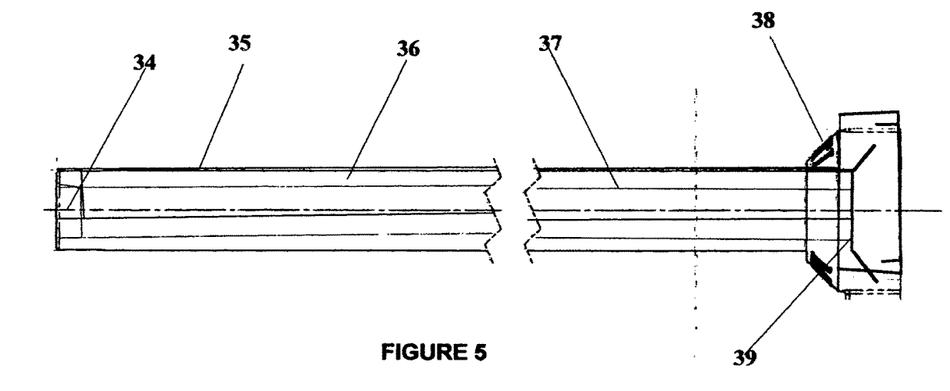
FIG. 5 is a lateral view of a reusable zero degree Illumination Adapter.

FIG. 5 is a lateral illustration of a reusable zero degree Illumination Adapter 2. The Illumination Adapter 2 slides over the telescope assembly 1 until the proximal end of the adapter 39 physically contacts the light halo 8, This occurs when the flange 38 interlocks to the telescope proximal assembly 13.

The Illumination Adapter 2, fiber optics are the length of the adapter 2 and are hermetically sealed at both ends. At the distal end a zero power lens 34 seals the inner diameter of the adapter. The inside and outside diameters of the adapter are constructed of stainless steel cylinders, 35 & 37 to cover the individual fiber optics 36 sandwiched between them. In another embodiment, these retainers may be constructed of other materials, be they metal or plastic.

Figure 6:
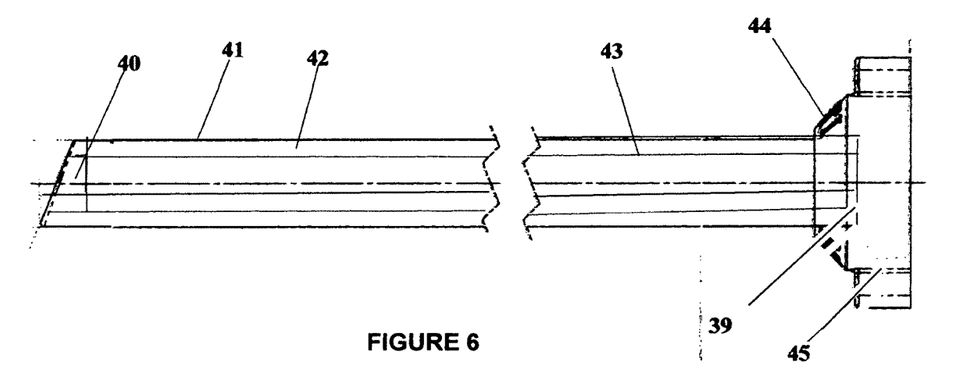
FIG. 6 is a lateral view of a reusable 30 degree Illumination Adapter.

FIG. 6 is a lateral illustration of the embodiment, of the Illumination Adapter 2 with a thirty (30) degree prism 40 sealing the distal end. In this embodiment, a compound prism 40 provides an off axis viewing angle of 30 degrees. A compound prism with the outer and inner surfaces are different as this is necessary to prevent the height of the prism 40 from interfering with the field of view of the telescope 1.

In an embodiment, the distal illumination fibers 42 are cut, ground and polished at the same angle as the prism 40. The proximal end 39 is polished flat and contacts the proximal light halo 8 on the proximal assembly 13. A large number of individual fiber are contained within the same stainless steel structure 41 & 43.

In an embodiment, the angled adapter is constructed with a flange assembly 44 with tabs 45 located preferably on the center line of the prism 40 to provide external visual orientation. The tabs 45 on the flange provide a means of continuously rotating the prism 40 through 360 degree of rotation. The flange assembly 44 also provides the means of retaining the adapter and for inserting and removing the adapter 2 from the telescope 1.

Figure 7:
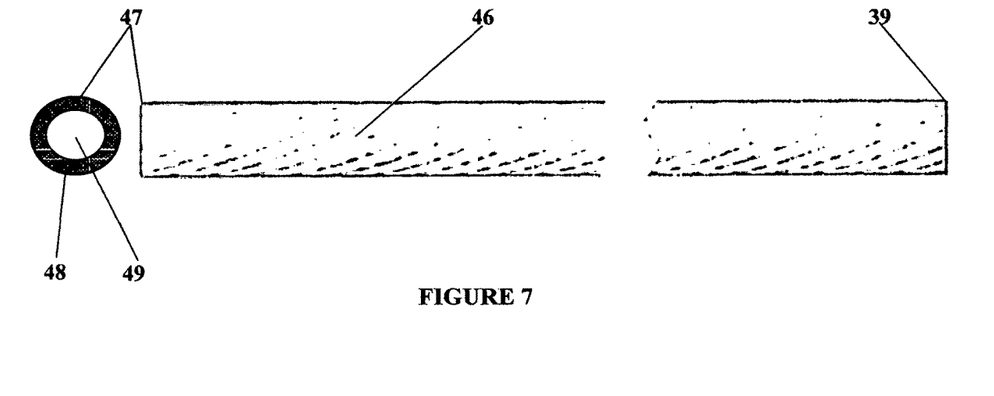
FIG. 7 is a lateral view of the disposable zero degree plastic lumen adapter.

FIG. 7 is a lateral view of the embodiment of the fiber optics bundle 46 used to construct the Illumination Adapter 2. The fibers are randomly wrapped along the length the inner diameter cylinder 48. The outer cylinder covers the exposed fiber assembly 47. The hollow core 49 slides over the telescope 1. The proximal end 39 contacts to the light halo 50. In an embodiment with the prism the fiber optics are constructed similar manner but surround the prism.

Figure 8:
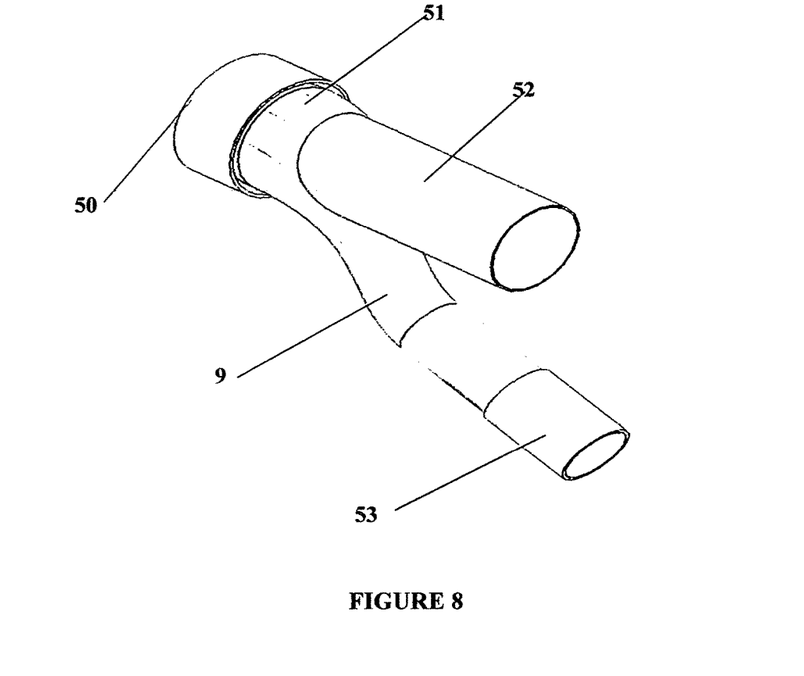
FIG. 8 is a lateral view of the disposable 30 degree plastic lumen adapter.

FIG. 8 is a orthogonal illustration of the embodiment of the proximal fiber optic assembly 9 contained inside of the proximal housing 13. The fiber optic elements 9 are wrapped around the telescope tube 52 and retained by a retaining ring 51. The individual fibers are cemented together and ground and polished to a smooth finish at both ends of the assembly. A second retainer 53, holds the entire bundle of fibers in a single grouping and are cemented together to form a solid assembly for insertion into the ferrule 10.

In an embodiment of a disposable fiber optic assembly 9, the light halo 50 is made up of molded cyclic polyolefin (Nippon Zeon 5000) an high transmission optical grade plastic in which one end surrounds the telescope tube 52. A preferred means of assembly is to cement two (2) elements of the plastic assembly 9 around the telescope tube and encapsulate the assembly in the proximal housing 39 and molded to fit the input to the ferrule.

Figure 9:
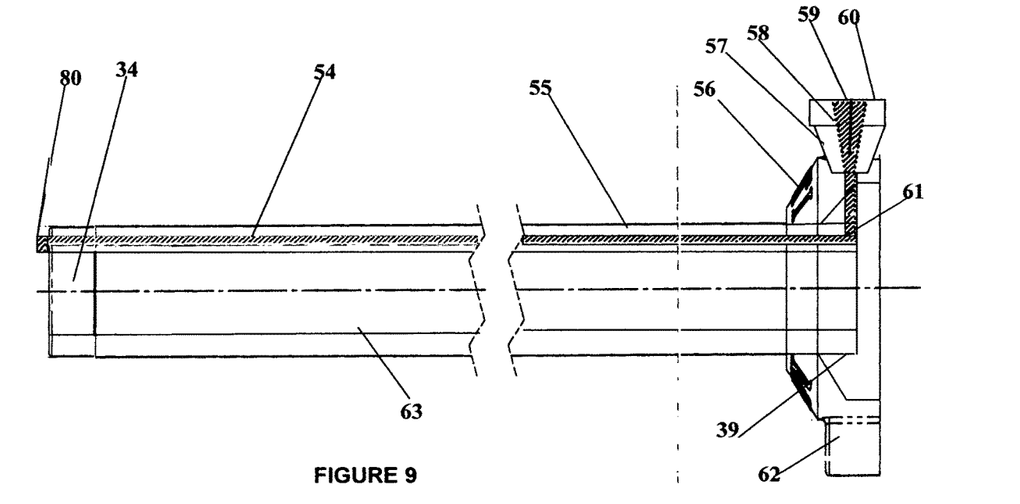
FIG. 9 is a lateral view of a disposable zero degree plastic lumen adapter with means for cleaning the distal objective lens.

FIG. 9 is a lateral view of the disposable zero degree plastic Lumen Adapter 2. In place of a stainless steel Illumination Adapter 2. Similarly, the disposable plastic Lumen Adapter 2 slides over the telescope assembly 1 until the proximal end 39 is in physical contact with the light halo 8 and interlocks with the flange 56 on the telescope 1 proximal assembly 31. The disposable Lumen Adapter is compatible with both the reusable or disposable telescope 1.

The embodiment of a lumen consists of a 10 mm outer diameter 55 and an inner diameter of approximately 8 mm 63. Co extruded between the inner and outer diameters 55 & 63 is a open pathway of approximately 0.5 mm in diameter 54 that runs the length of the lumen.

In the embodiment, the adapter 2 is constructed to transmit light from the proximal end 39 to the distal end 81. The lumen 55 is also designed to clean blood and tissue from the distal lens 34 without removing the laparoscope from the body. In a preferred embodiment a cleaning solution such as Saline or other cleaning liquid is injected, with a syringe into the slot 59 in the diaphragm assembly 56 and into the stainless steel tube 61 that interfaces with the 0.5 mm pathway 54 into the body. The flange assembly 56 consisting of 57, 58, 59 60 & 61 create a means of injecting the saline into the collapsible opening slot 59 in the proximal flange assembly 56 and conveys the cleaning solution into the 0.5 mm pathway 54 and have it exit at a diffuser 80 at the distal end.

In practice, as the fluid displaces the air that is in the 0.5 mm pathway 54, air pressure is built up as fluid replaces the air creating an air flow over the lens to blow away particulate that may have attached itself to the lens 34. In the embodiment, air and fluid act in sequence under pressure by the action of a syringe.

In an embodiment, a retainer 58, holds a polyurethane membrane 58 captured inside of the retainer 58 and held under compression. The membrane 58 is slit 59 to allow a syringe to be inserted through the membrane 58 allowing access to the stainless steel tube 61 that allows access to the 0.5 mm pathway 54 transiting the length of the lumen 55. The membrane 58 encapsulates the syringe, preventing back flow from the pressure exerted by the syringe. In an embodiment, the flange 56 provides a means of locking the adapter 55 in place and a molded tab 62 provides a means of rotating the assembly to a convenient place to inject the fluid.

Figure 10:
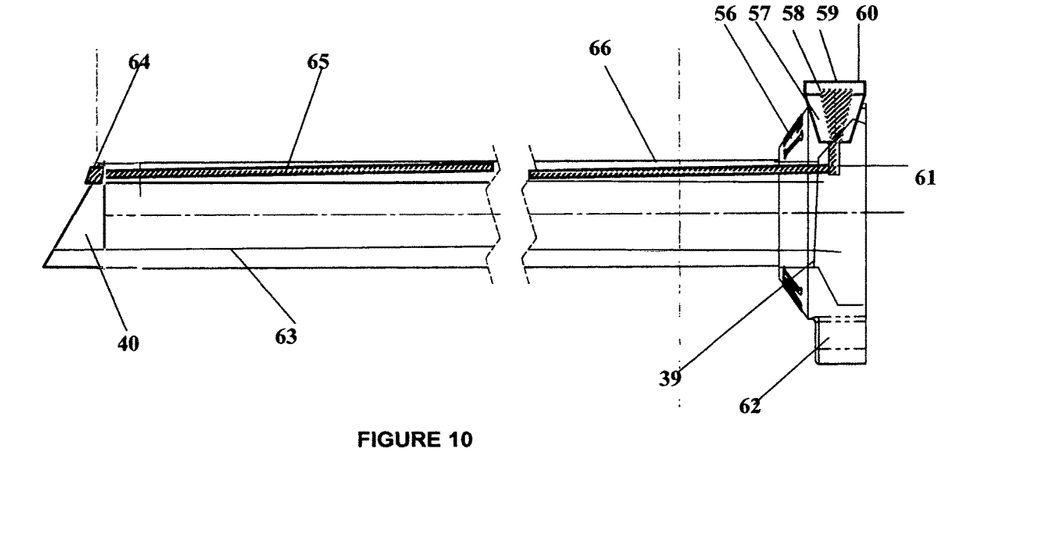
FIG. 10 is a lateral view of a disposable 30 degree plastic lumen adapter with provisions for cleaning the distal objective prism.

FIG. 10 is a lateral view that illustrates the embodiment of the angled version of the disposable Lumen Adapter 2. A 30 degree cylindrical prism 40 at the distal end is surrounded by the plastic illumination cylinder 66 used to transmit light from the light halo 8 into the body cavity. The diffuser 64 is at the same angle as the prism 40 to disperse the air and saline over the surface of the prism 40 and angled lumen 66. An embodiment of the flange 56 assembly as a means of injecting saline with a syringe uses the same assembly of 56, 57, 58, 59, 60 and 61 make up the embodiment of the injector mechanism.

The flange 56 and the tab 62 serve two purposes. The flange 56 enables 360 degrees of continuous rotation of the prism around the lens tube 11 to provide a means of viewing a circular area in the body cavity corresponding with the field of view of the telescope as defined by the prism 40. The rotation also provides a means of positioning the membrane 58 to insert a syringe containing saline.

Figure 11:
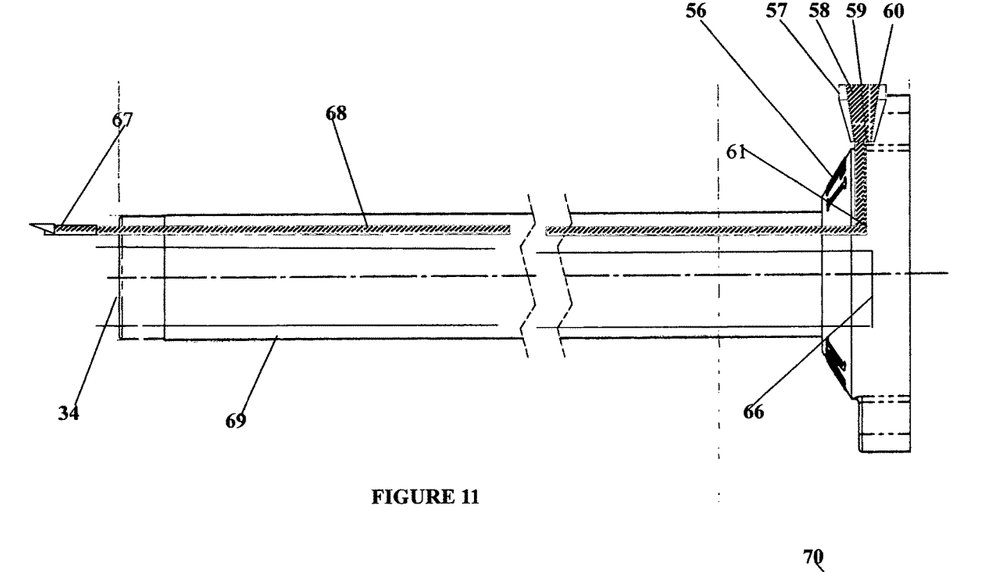
FIG. 11 is a lateral view of a disposable zero degree plastic lumen adapter with provisions for injecting drugs distally into the body from a proximal insertion source.

FIG. 11 is a lateral view of an illustration of an embodiment of a disposable Lumen with a syringe 67 located at the distal end of the lumen 68. The lumen 68 and the telescope 1, in an embodiment, allows a surgeon to view where a drug is to be injected. Once a determination is made, a syringe located at the proximal end is inserted through a slit 59 in the poly urethane membrane 58 into the path way 61 into the body cavity. The syringe is depressed until the air is removed from the lumen and the drug is present at the distal hypodermic needle 67. This is visualized in the body through the telescope 1. The hypodermic needle at the distal end 67 is then injected into the tissue at a location determined by the surgeon as it is monitored through the telescope 1. Upon completion of the the injection, the telescope 1 and drug lumen 68 are removed from the body cavity.

Figure 12:
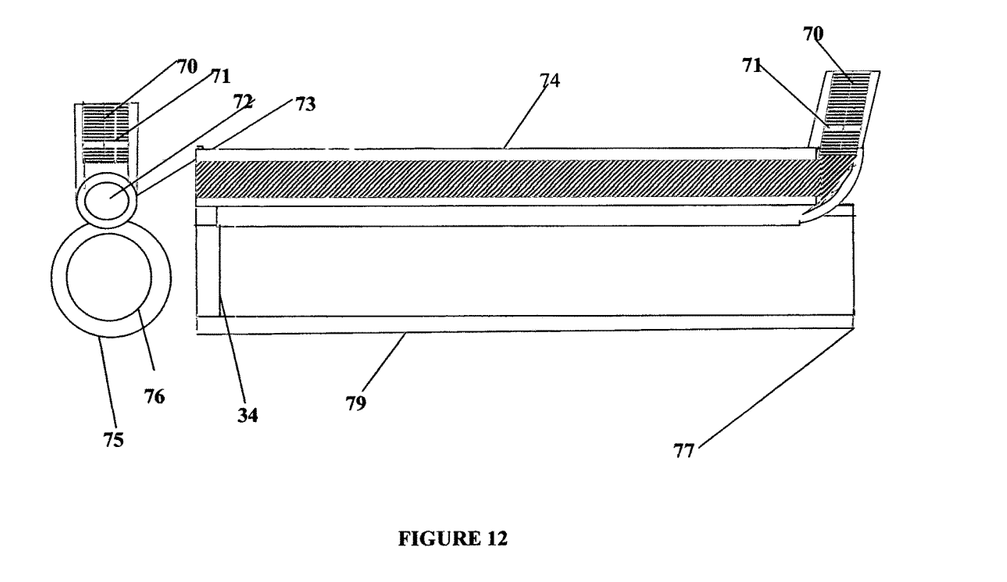
FIG. 12 is a lateral view of a disposable plastic lumen adapter with working channels for laser and surgical therapy.

FIG. 12 is lateral view of an illustration of an embodiment of a disposable Lumen Adapter for use with a working channel A second lumen 74 provides a working channel whose diameter is determined for the specific surgical function. For example; a Lumen Adapter can guide a fiber optic that carries a laser fiber, a surgical cutting tool, cauterization device or stapling device. The laser fiber optic or surgical tool enters through a diaphragm 71 through the length of the lumen 74 and beyond. The laser fiber or working device are visually directed from the telescope 1. The diameter of the combined lumens 74 and 79 has sufficient clearance to transit a trocar opening. Once a procedure has been completed and the therapeutic device is removed from the body, the lumen can then also be used to evacuate smoke, solids or fluids from the body by connecting a evacuation system to the lumen's diaphragm 71 and exit port 70.

While the Bala Laparoscope System has been particularly shown and described with references to the preferred embodiment thereof, it will be understood by those skilled in the art that various changes in form and details, may be made therein without departing from the spirit and scope of the inventions that is defined by the appended claims.

What is claimed is:

1. A laparoscope comprising:
    a telescope tube having a proximal end and a distal end;
    a first achromatic doublet lens provided in the telescope tube at the distal end;
    a first singlet lens provided in the telescope tube adjacent to the first achromatic doublet lens;
    a field stop provided in the telescope tube adjacent to the first singlet lens;
    a second singlet lens provided in the telescope tube adjacent the proximal end;
    a second achromatic doublet lens provided in the telescope tube between the first achromatic doublet lens and the second singlet lens; and
    a third singlet lens provided in the telescope tube between the field stop and the second achromatic doublet lens.

2. The laparoscope of claim 1, further comprising:
    a housing provided at the proximal end of the telescope tube;
    a video camera mount attached to the housing; and
    a focusing assembly configured to move relative to the housing to provide focusing of an image from the telescope tube.

3. The laparoscope of claim 1, wherein each of the lenses is provided with an anti-reflection coating.

4. The laparoscope of claim 1, further comprising:
    a housing provided adjacent the proximal end of the telescope tube;
    an eyepiece assembly connected to the housing to view an image from the telescope tube; and
    a third achromatic doublet lens provided within the eyepiece assembly.

5. The laparoscope of claim 1, further comprising:
    a ferrule provided on the proximal end of the telescope tube having an assembly of bundled fibers configured to transmit light from an external source to a ring of fibers around the telescope tube at the proximal end.

6. The laparoscope of claim 5, wherein the ring of fibers provides a light halo at the proximal end of the telescope tube.

7. The laparoscope of claim 6, further comprising:
an illumination adapter configured to slide over the telescope tube, the illumination adapter having a distal end and a proximal end, wherein the proximal end of the illumination adapter physically contacts the light halo.

8. The laparoscope of claim 7, wherein the illumination adapter is a zero degree illumination adapter.

9. The laparoscope of claim 7, further comprising:
a compound prism at the distal end of the illumination adapter to provide an off-axis viewing angle, the compound prism being configured to rotate three hundred sixty degrees.

10. The laparoscope of claim 9, wherein the viewing angle is thirty degrees.

11. A laparoscope system, comprising:
a telescope tube having a proximal end and a distal end;
a plurality of lenses provided in the telescope tube to convey an image from a distal end of the telescope tube to a proximal end of the telescope tube;
a light halo provided around an outer diameter of the telescope tube at the proximal end of the telescope tube;
a first illumination adapter separate from and configured to slide over the telescope tube, a proximal end of the first illumination adapter configured to physically contact the light halo;
a second illumination adapter separate from and configured to slide over the telescope tube, a proximal end of the second illumination adapter configured to physically contact the light halo; and
a compound prism at a distal end of the second illumination adapter configured to provide an off-axis viewing angle.

12. The laparoscope system of claim 11, wherein the viewing angle provided by the compound prism is thirty degrees.

13. The laparoscope system of claim 11, wherein the compound prism is configured to rotate three hundred sixty degrees.

14. The laparoscope system of claim 11, wherein the first illumination adapter further comprises:
a hollow core configured to slide over the telescope tube;
an inner diameter surrounding the hollow core;
an outer diameter; and
a fiber optics bundle between the inner diameter and outer diameter, the fiber optics bundle configured to provide light to the telescope tube from the light halo.

* * * * *